(12) United States Patent
Rozzell, Jr. et al.

(10) Patent No.: US 7,081,535 B2
(45) Date of Patent: Jul. 25, 2006

(54) HYDROXY-AMINO ACIDS

(75) Inventors: J. David Rozzell, Jr., Burbank, CA (US); Spiros Kambourakis, Pasadena, CA (US)

(73) Assignee: BioCatalytics, Inc., Pasadena, CA (US)

( * ) Notice: Subject to any disclaimer, the term of this patent is extended or adjusted under 35 U.S.C. 154(b) by 0 days.

(21) Appl. No.: 11/014,423

(22) Filed: Dec. 16, 2004

(65) Prior Publication Data

US 2005/0100993 A1    May 12, 2005

Related U.S. Application Data

(63) Continuation of application No. 10/237,831, filed on Sep. 9, 2002, now Pat. No. 6,833,471.

(51) Int. Cl.
| | | |
|---|---|---|
| *C07D 211/70* | (2006.01) | |
| *C07D 211/82* | (2006.01) | |
| *C07D 213/55* | (2006.01) | |
| *C07D 333/22* | (2006.01) | |
| *C07C 229/00* | (2006.01) | |

(52) U.S. Cl. .................. 546/335; 549/76; 562/444; 562/567

(58) Field of Classification Search ................ 562/444, 562/567; 546/335; 549/76
See application file for complete search history.

(56) References Cited

OTHER PUBLICATIONS

Osterberg, A. The Synthesis of Two Hydroxylaminovaleric Acids, α-amino-β-hydroxy- and γ-amino-βhydroxyvaleric Acids Journal of the American Chemical Society, vol. 49(2), pp. 538-540 (1927).*
Cavallo and Khiar, "Synthesis of (2S,3R)-3-Amino-2-hydroxy-5-methylhexanoic Acid: Bridging Efect of KF" Journal of Organic Chemistry, vol. 55, pp. 4750-4754 (1990).*
Harbeson et al, "Stereospecific Synthesis of Peptidyl α-Keto Amides as Inhibitors of Calpain" Journal of Medicinal Chemistry, vol. 37, pp. 2918-2929 (1994).*
Andrés et al, "Diastereoselective Synthesis of Enantiopure γ-amino-β-hydroxy Acids by Reformatsky Reaction of Chiral α-Dibenzylamino aldehydes" Tetrahedron, vol. 57, pp. 8521-8530 (Oct. 1, 2001).*
Halling et al, "Synthesis of DL-Statine and DL-4-Amino-3-hydroxy-4-phenylbutanoic Acids via the Oxazoline Route" Acta Chemica Scandanavica, vol. 45(7), pp. 736-741 (1991).*
Bolte, A., et al.; *Bakers' Yeast Reduction of an Acrylic β-diketone*; Reduction Reactions of Aliphatic Ketone (2:3:10 through 2:3.15); ©1993 by John Wiley & Sons Ltd., Update 1; 6 sheets.

Sakai, R., et al., Structure-Activity Relationships of the Didemnins, J. Med. Chem., 1996, vol. 39, No. 14, pp. 2819-2834.
Stratmann, K., et al., Hapalosin, a Cyanobacterial Cyclic Depsipeptide with Multidrug-Resistance Reversing Activity, J. Org. Chem., 1994, vol. 59, pp. 7219-7226.
Almond, M., et al., Hofmann Rearrangement Under Mildly Acidic Conditions Using [*I,I-Bis (Trifluoroacetoxy)*] *Iodobenzene: Cyclobutylamine Hydrochloride* from *Cyclobutanecarboxamide*, Organic Syntheses, CV 8, 132, pp. 1-3 (Nov. 21, 2001).
Arslan, T. and Benner S.A., Reduction of 2-Substituted 3-Oxoglutarates Mediated by Baker's Yeast. Variation in Enantioselectivity without Corresponding Variation in Diastereoselectivity, J. Org. Chem. 1993, vol. 58, pp. 2260-2264.
Boger, D.L., et al., Total Synthesis of Bleomycin $A_2$ and Related Agents. 1. Synthesis and DNA Binding Properties of the Extended C-Terminus: Tripeptide S, Tetrapeptide S, Pentapeptide S, and Related Agents, J. Am. Chem Soc., 1994, vol. 116, pp. 5607-5618.
Castejon, P., et al. Ready Access to Stereodefined βHydroxy-γ-amino Acids. Enantioselective Synthesis of Fully Protected Cyclohexylstatine, Tetrahedron, vol. 52, No. 20. pp. 7063-7086 (1996).
Catasus, M., et al., A Totally Stereocontrolled Route to N-Methyl-γ-amino- β-hydroxy Acids: Asymmetric Synthesis of the Amino Acid Component of Hapalosin, Tetrahedron Letters, 1999, vol. 40, pp. 9309-9312.
Didier, E., et al. Chemo-Enzymatic Synthesis of 1,2- and 1,3- Amino-Alcohols and Their Use in the Enantioselective Reduction of Acetophenone and Anti-Acetophenone Oxime Methyl Ether with Borane, Tetrehedron, vol. 47 No. 27, pp. 4941-4957 (1991).
Dinh, T.Q., and Armstrong, R.W., A Convergent Total Synthesis of the Multidrug Resistance-Reversing Agent Hapalosin, J. Org. Chem. 1995, vol. 60, pp. 8118-8119.
Hamada Y., et al., Efficient Total Synthesis of Didemnins A and B, J. Am. Chem Soc., 1989, vol. 111, pp. 669-673.
Hoffman, R.V. and Tao, J., An Improved Anantiospecific Synthesis of Statine and Statine Analogs via 4-(N,N-Dibenzylamino)-3-keto Esters, J. Org. Chem. 1997, vol. 62, pp. 2292-2297.

(Continued)

*Primary Examiner*—James O. Wilson
*Assistant Examiner*—Zachary C. Tucker
(74) *Attorney, Agent, or Firm*—Christie, Parker & Hale, LLP

(57) ABSTRACT

Hydroxy-amino acids are provided and are prepared by contacting a substituted β-ketodiester having a ketone group and two ester functional groups with a ketoreductase under conditions permitting the reduction of the keytone group to an alcohol. Only one of the ester functional groups is regioselectively hydrolyzed to the corresponding carboxylic acid, whereby a non-hydrolyzed ester functional group remains. The carboxylic acid is converted to an amine to produce a hydroxy-amino acid.

9 Claims, No Drawings

OTHER PUBLICATIONS

Jones, J.B. and Takemura T., Enzymes in organic synthesis. 30. Reaction conditions—control of enantiomeric purities. Horse liver alcohol dehydrogenase-catlayzed reductions of 2-alkylcyclohexanones and their thiopyran analogs, Can. J. Chem, 1984, vol. 62, pp. 77-80.

Kazmaier, U. and Krebs, A., A Straightforward Synthesis of Protected Isostatine from Achiral Precursors using the Asymmetric Chelate Claisen Rearrangement, Tetrahedron Letters, 1999, vol. 40, pp. 479-482.

Kinoshita, M. and Masaki, A., Synthetic Studies of Pyridomycin. II. Synthesis of a Model Twelve-membered Ring Compound Related to Pyridomycin, Bulletin of the Chemical Society of Japan, 1978, vol. 51(3), pp. 869-871.

Kwon, J.K and KO, S.Y., Synthesis of statine employing a general syn-amino alcohol building block, Tetrahedron Letters, 2002, vol. 43, pp. 639-641.

Li, W.R., et al., Total Synthesis and Structural Investigations of Didemnins A, B, and C, J. Am. Chem. Soc., 1990, vol. 112, pp. 7659-7672.

Maibaum, J. and Rich, D.H., A Facile Synthesis of Statine and Analogues by Reduction of β-Keto Esters Derived from Boc-Protected Amino Acids. HPLC Analyses of Their Enantiomeric Purity, J. Org. Chem. 1988, vol. 53, pp. 869-873.

Ninomiya, K., et al., Amino Acids and Peptides, XII Phosphorus in Organic Synthesis. VIII Reaction of Malonic Acid Half Esters with Diphenyl Phosphorazidate, Chem. Pharm. Bull, 1974, vol. 22, pp. 1398-1404.

Reddy, G.V., et al. A Novel Wittig Reaction of Oxazolidinones: Stereospecific Synthesis of N-BOC-(3S,4S)-Statine and N-BOC-(3S,4S)-AHPPA, Tetrahedron Letters, 1999, vol. 40, pp. 775-776.

Rich, D.H., et al., Synthesis of Analogues of the Carboxyl Protease Inhibitor Pepstatin. Effect of Structure on Inhibition of Pepsin and Renin, J. Med. Chem., 1980, vol. 23, pp. 27-33.

Rodriguez, S., et al., Asymmetric Synthesis of β-Hydroxy Esters and α-Alkyl-β-hydroxy Esters by Recombinant *Escherichia coli* Expressing Enzymes from Baker's Yeast, J. Org. Chem., 2000, vol. 65, pp. 2586-2587.

Sakai, R., et al., Seven New Didemnins from the Marine Tunicate *Trididemnum solidum*, J. Am. Chem. Soc., 1995, vol. 117, pp. 3734-3748.

Sakai, R., et al., Structure-Activity Relationships of the Didemnins, J. Med. Chem., 1996, vol. 39, pp. 2819-2834.

Shiori, T., et al., Stereoselective Synthesis of Dolastatin 10 and Its Congeners, Tetrahedron, 1993, vol. 49, No. 9, pp. 1913-1924.

Stratmann, K., Hapalosin, a Cyanobacterial Cyclic Depsipeptide with Multidrug-Resistance Reversing Activity, J. Org. Chem. 1994, vol. 59, pp. 7219-7226.

Umezawa, H., et al., Pepstatin, a new Pepsin Inhibitor Produced by Actinomycetes, The Journal of Antibiotics, May 1970, vol. XXIII No. 5., pp. 259-262.

Veeresha, G. and Datta, A., Stereoselective Synthesis of (-)-N-Boc-Statine and (-)-N-Boc-Norstatine, Tetrahedron Letters, 1997, vol. 38, No. 29, pp. 5223-5224.

Yoo, D., et al., The N-Hydroxymethyl Group for Stereoselective Conjugate Addition: Application to the Synthesis of (-)-Statine, Organic Letters, 2002, vol. 4, No. 7, pp. 1213-1215.

* cited by examiner

HYDROXY-AMINO ACIDS

CROSS-REFERENCE TO RELATED APPLICATION

This application is a Continuation, and claims priority, of U.S. application Ser. No. 10/237,831, filed Sep. 9, 2002, now U.S. Pat. No. 6,833,471 the entire contents of which are incorporated by reference herein.

FIELD OF THE INVENTION

This invention relates to methods for the production of chiral compounds, and in particular to methods for the production of chiral hydroxy-amino compounds. The hydroxy-amino compounds have applications in the synthesis of pharmaceutical products.

BACKGROUND

Natural and non-natural α-hydroxy-β-amino acids and β-hydroxy-γ-amino acids and their derivatives occur in many biologically active natural products and are important intermediates in the synthesis of various pharmaceuticals. One of the most important α-hydroxy-β-amino acids is the side chain of the potent anticancer drug Taxol. Various derivatives of this β-amino acid have been synthesized and linked to the polycyclic core ring of Taxol in an effort to improve the potency and the spectrum of uses of this important drug.

The β-hydroxy-γ-amino acid structural motif is encountered in a number of natural products and current and developmental drugs. Some of the most common β-hydroxy-γ-amino acids include statine, isostatine and benzyl statine (phenylstatine) (FIG. 1). Statine is the key component of pepstatin, a naturally-occurring hexapeptide antibiotic, which acts as an inhibitor of aspartic acid proteases such as rennin, pepsin and cathepsin D [Umezawa, H et al J. Antibiotics 23, 259 (1970); Ric, D. H. J. Med. Chem 23, 27 (1980)]. The low selectivity of pepstatine has led to the development of more specific synthetic analogues by substituting the isobutyl moiety of statine with more lipophilic substituents such as cyclohexylmethyl, which led to the widely used analogue cyclohexyl-statine. Isostatine is an essential amino acid in Didemnins [Sakai, R. at al J. Am. Chem. Soc. 117, 3734 (1995); Joullie, M. M. J. Am. Chem. Soc 112, 7659 (1990)), a group of cyclic peptides which show strong antitumor, antiviral, and immunosuppressive activity (Sakai, R. et al. J. Med. Chem. 39, 2819 (1996)]. Benzyl statine is part of the biologically active compounds hapalosin (Stratmann, K et al J. Org. Chem. 59, 7219 (1994); Armstrong, R. W. J. Org. Chem. 60, 8118, (1995)] and dolastatin 10 [Shiori, T et al Tetrahedron 49, 1913 (1993)]. In particular hapalosin restores the lethal activity of cytotoxic antitumor drugs (such as actinomycin D, colchicines and taxol) to cancer cells by breaking the β-glycoprotein-mediated multi-drug resistance caused by the export of the cancer drugs from the cell using transmembrane P-glycoproteins.

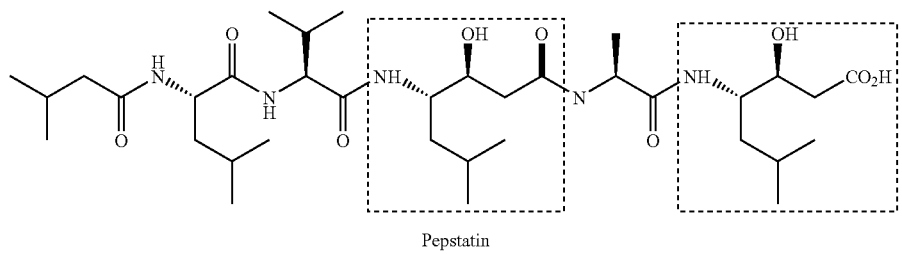

Pepstatin

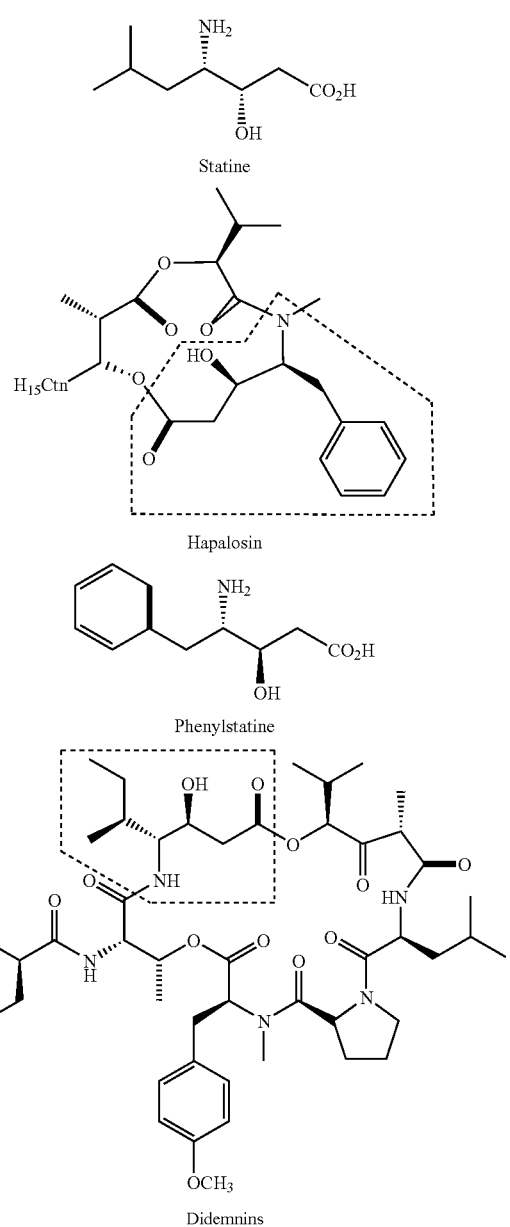

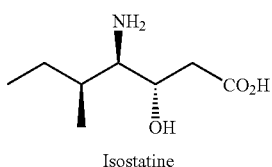

Figure 1: Natural products and related pharmaceuticals that contain γ-amino-β-hydroxy amino acids.

Other β-hydroxy-γ-amino acids that are incorporated in molecules with biological activities include (2S,3S,4R)-4-amino-3-hydroxy-2-methyl pentanoic acid, which is the amino acid linker of bleomycin B2 and the main constituent of the powerful carcinostatic blenoxane [Boger, D. L et al *J. Am Chem Soc* 116, 5607, (1994)] and (2R,3S,4R)-4-amino-3-hydroxy-2-methyl-5-(2'-pyridil) pentanoic acid, which is part of pyridomycin [Kinoshita, M; Awamura, M. *Bull. Chem. Soc* 51, 869 (1978)], a Streptomyces-synthesized anti-mycobacterial drug (Figure 2). Statines and related compounds based on β-hydroxy-γ-amino acids are particularly prevalent in anti-cancer drugs and drug candidates. The absolute stereochemistry of these molecules is important for biological activity.

b Figure 2: Potent biologically-active natural products that contain γ-amino- β-hydroxy amino acids.

Another important motif in pharmaceutically-active compounds is the α-hydroxy-β-amino acid structural unit. Among the examples of pharmaceutical products that contain the α-hydroxy-β-amino acid moiety as a key component in their structures are molecules such as bestatin, amastatin and ubenimex, which possess immunoregulatory, antitumor and antimicrobial activities. The ability to prepare compounds in this class with defined absolute stereochemistry is critical to the commercial synthesis of these compounds and their analogs.

Despite the general importance of hydroxyl-substituted β- and γ-amino acids and their derivatives as pharmaceutical intermediates, the preparation of these compounds remains a significant challenge to chemists. Most of the synthetic approaches toward the production of α-hydroxy-β-amino acids are purely chemical transformations that require multi-step reaction sequences, chiral catalysts or starting materials, and stringent or air-sensitive reaction conditions. Occasionally the synthetic methods involve the production of relatively unstable intermediates. Most of the chemical syntheses of statine and isostatine, for example, begin from the natural α-amino acids leucine and isoleucine, respectively [Hamada, Y. et al *J. Am Chem Soc,* 111, 669 (1989); Tao, J.; Hoffmann, R. V *J. Org. Chem* 62, 2292 (1997)]. After protection of the amino group (PG=protecting group), an aldol or Claisen condensation to the β-keto-γ-amino acid followed by a reduction gives the desired β-hydroxy γ-amino acid product (FIG. 3).

Figure 3: Outline of the most common current chemical syntheses of β-hydroxy-γ-amino acids.

Some of the problems encountered in these syntheses are the isomerization of the γ-carbon under the basic conditions of the condensation reaction, the many steps required (often 7–10), and the low diastereoselectivity of the final reduction step, which often times gives the wrong diastereomer as the major product [Kessler, H; Schudok, M *Synthesis* 457 (1990); Maibaum, J.; Rich, D. H *J. Org. Chem* 53, 869 (1988)]. An obvious drawback in using methods based on natural amino acid precursors for the synthesis of β-hydroxy-γ-amino acids is that non-natural α-amino acid counterparts cannot always be easily accessed, and for this reason other chemical synthetic schemes have been developed. The β,γ-amino alcohol moiety in one alternative synthetic route is synthesized from α,β-unsaturated alcohols that are epoxidized using a chiral catalyst, followed by a ring opening using an nitrogen nucleophile (FIG. 3) [Catasus, M. et al *Tetrahedron Lett* 40, 9309 (1999); Catejon, P. et al *Tetrahedron* 52 7063. (1996)]. Although good enantiomeric purity of the product was reported (90–99% ee), this methodology is long (6–10 steps), gives moderate yields (20–40%), and requires expensive catalysts and stringent air-sensitive reaction conditions. Other methods for synthesizing β-hydroxy-γ-amino acids involve Wittig reactions of chiral oxazolidinones [Reddy, G. V et al *Tetrahedron Lett* 40, 775 (1999)] asymmetric Claisen rearrangements [Krebs, A.; Kazmaier, U. *Tetrahedron Lett.* 40, 479 (1999)], selective Grignard reaction of N-protected amino acids [Veeresha, G.; Datta, A *Tetrahedron Lett* 38, 5223 (1997)] or the use of doubly chiral precursors [Kwon and Ko, *Tetrahedron Lett* 43, 639–641 (2002)]. Again, long and complicated reaction sequences and chiral starting materials and/or catalysts are required using these methodologies.

Enzyme catalysis offers an alternative to purely chemical synthetic schemes. Enzymatic methods that have been reported to date are resolutions of a racemic mixture, having a maximum yield of 50% for the resolution step alone. Challenges similar to those encountered in the chemical synthesis of β-hydroxy-γ-amino acids are also faced in the chemical synthesis of α-hydroxy-γ-amino acids. In both cases, gaining control over the stereochemistry of the chiral carbons bearing both the amino and the alcohol groups at reasonable cost and high enantiomeric purity is the key to the successful production of these important chemical intermediates.

Chiral hydroxy compounds can be produced by the stereoselective reduction of ketones catalyzed by ketoreductase enzymes. As used herein, the term ketoreductase means any enzyme that catalyzes the reduction of a ketone to form the corresponding alcohol. Ketoreductase enzymes include those classified under the Enzyme Commission numbers of 1.1.1. Such enzymes are given various names in addition to ketoreductase, including, but not limited, to alcohol dehydrogenase, carbonyl reductase, lactate dehydrogenase, hydroxyacid dehydrogenase, hydroxyisocaproate dehydrogenase, β-hydroxybutyrate dehydrogenase, steroid dehydrogenase, sorbitol dehydrogenase, aldoreductase, and the like.

Many examples of enzymatic reductions of various classes of substrates have been reported [Wong, C-H; Whitsides, G. M. *Enzymes in Synthetic Organic Chemistry*, Pergamon, New York, (1994); Sugai, T *Curr. Org. Chem* 3, 373 (1999)]. Various alcohol dehydrogenases have been investigated [Patel, R. N *Adv. Appl. Microbiol* 43, 91 (1997); Riva, S.; Carrea, G. *Angew. Chem. Int. Ed* 39, 2226 (2000)]. A well known example is horse liver alcohol dehydrogenase (HLADH), an enzyme that has been very extensively studied and can reduce aldehydes and ketones to the corresponding alcohols, in some cases providing alcohols in good enantiomeric purity. The substrate range is limited and does not include most β-ketoesters, however.

Various ketoreductase enzymes have been identified that catalyze the stereoselective reduction of a range of different ketones, including β-ketoesters. [See, for example, J. David Rozzell, ACS Symposium Series 776, Applied Biocatalysis in Specialty Chemicals and Pharmaceuticals, B. C. Saha and D. C. Demirjian, eds., pp.191–199, (2000) and references therein, all hereby incorporated by reference.] These enzymes have been shown to act on a number of structurally diverse ketones. The genes expressing a number of these broad-range ketoreductases have been cloned and expressed, and a number of these enzymes are readily available commercially (BioCatalytics, Inc, Pasadena, Calif. USA). In many cases, enzymes can be identified that can produce either stereoisomer of a chiral alcohol by stereoselective reduction of a target ketone. For example, when the Ketoreductase Screening Set (Catalog number KRED-8000, BioCatalytics, Inc, Pasadena, Calif. USA) containing 8 different ketoreductases was screened against either alpha-chloroacetophenone or ethyl 4-chloroacetoacetate, some enzymes could be found within the set that were R-selective while others were found that were S-selective with respect to the chiral alcohol produced.

It has also been demonstrated that ketoreductase enzymes can be used to catalyze the reduction of 2-substituted-3-ketoesters. The products of these reductions are compounds with two chiral centers, and depending on the enzyme employed, the reduction can be diastereoselective, as shown in FIG. 4. Such reactions have been described using isolated enzymes and with whole cells. When the enzymes within the Ketoreductase Screening Set (Catalog number KRED-8000, BioCatalytics, Inc, Pasadena, Calif. USA) were studied for the reduction of 2-ethyl-3-ketobutyrate ethyl ester, certain enzymes were shown to be highly diastereoselective for the reduction to the corresponding alcohol. [For other examples, see S. Rodriguez et al., *J. Org. Chem.*, 65, 2586 (2000); S. Rodriguez et al., *J. Am. Chem. Soc.*, 123, 1547 (2001) and references therein, hereby incorporated by reference.]

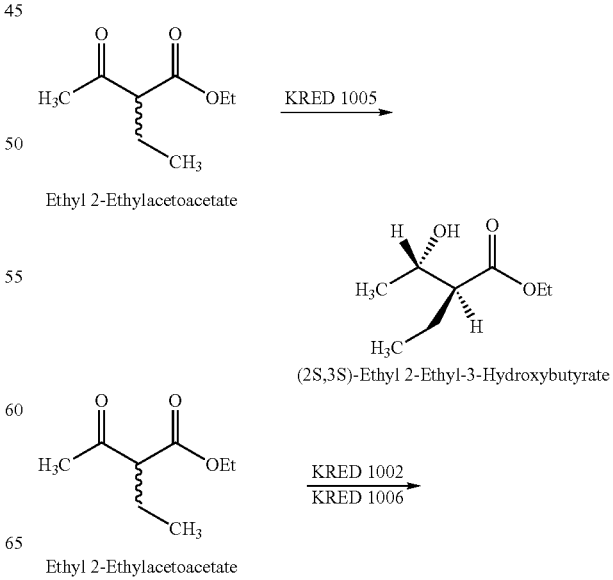

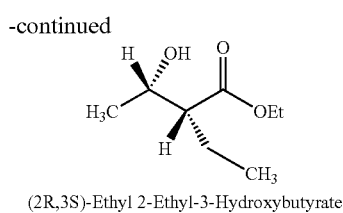

(2R,3S)-Ethyl 2-Ethyl-3-Hydroxybutyrate

Figure 4: Diastereoselective reduction of 2- substituted-3-ketoesters

In contrast to the 2-substituted-3-ketoesters shown in FIG. 4, there is only a single report of the diastereoselective reduction of a β-ketodiester such as that depicted in FIG. 5.

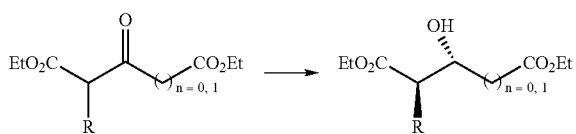

Figure 5: Diastereoselective reduction of β-ketodiesters

Benner and coworkers used actively fermenting Baker's yeast to carry out the reduction of the compounds shown in FIG. 5 where n is 1 and R is allyl or propargyl [T. Arsian and S. A. Benner, J. Org. Chem., 58, 2260–2264 (1993) and references therein, hereby incorporated by reference]. These compounds were prepared as potential precursors for the synthesis of non-standard nucleic acid bases. These were the only compounds for which reduction with fermenting yeast was reported, and the ketoreductase or ketoreductases involved were neither isolated nor determined. The reduction reaction was reported to be enantioselective and diastereoselective, although the degree of selectivity observed varied widely depending on reaction conditions, and yields in some cases were diminished by the partial metabolism of the substrate.

There are no reports of the highly diastereoselective reduction of a range of substituted β-ketodiesters, nor any reports of the use of substituted β-ketodiesters in the production of α-hydroxy-β-amino acids and β-hydroxy-γ-amino acids using a reaction sequence incorporating a diasereoselective reduction of substituted β-ketodiesters.

DESCRIPTION OF THE INVENTION

The present invention is directed toward methods for the production of hydroxy-amino acids in general, and to the production of α-hydroxy-β-amino acids and β-hydroxy-γ-amino acids in particular. The methods of the present invention are broadly applicable for the synthesis of a wide range of chiral hydroxy β- and γ-amino acids from inexpensive and easily accessible starting materials.

In one embodiment, the invention is directed to a method for producing a hydroxy-amino acid or a derivative thereof. A substituted β-ketodiester having a ketone group and two ester fuctional groups is contacted with a ketoreductase under conditions permitting the reduction of the ketone group to an alcohol. Only one of the ester functional groups is regioselectively hydrolyzed to the corresponding carboxylic acid, whereby a non-hydrolyzed ester functional group remains. Either the carboxylic acid or the non-hydrolyzed ester functional group is converted to an amine or a derivative thereof to produce a hydroxy-amino acid or derivative thereof.

A key step in the preparation of the target compounds is the diastereoselective reduction of substituted B-ketodiesters to form the corresponding substituted hydroxydiesters. In one embodiment, the method of the present invention uses a reaction sequence comprising a diastereoselective enzyme-catalyzed reduction of a β-ketodiester to introduce two or more chiral centers in a single step, followed by regioselective hydrolysis of only one of the two ester functional groups to form the corresponding carboxylic acid, and a conversion including a stereospecific chemical rearrangement in which the carboxylic acid is converted to an amine, or derivative thereof, to generate the desired hydroxy-amino acid, or derivative thereof. In another embodiment, the method of the present invention uses a reaction sequence comprising a diastereoselective enzyme-catalyzed reduction of a β-ketodiester, followed by regioselective hydrolysis of only one of the two ester functional groups to form the corresponding carboxylic acid, the conversion of the non-hydrolyzed ester functional group to an amide, a hydrazide, or a hydroxamic acid derivative, and a stereospecific chemical rearrangement in which the amide, hydrazide, or hydroxamic acid derivative is converted to an amine, or derivative thereof, to generate the desired hydroxy-amino acid, or derivative thereof. As used herein, as it pertains to a hydroxyamino compound, the words "derivative thereof" means a carbamate or urethane, which can be cyclic or acyclic, a urea, a hydrazide, or an amide formed from the amino group, or any protected form of the alcohol, including ethers, silyl ethers, alkyl esters, aryl esters, aralkyl esters, or carbonate esters.

In connection with this invention, it has been discovered that, when contacted with an appropriate ketoreductase, a broad range of substituted β-ketodiesters, such as 3-substituted-oxaloacetic diesters (n=0 in FIG. 5) and 2-substituted-3-ketoglutarate diesters (n=1 in FIG. 5), can be reduced diastereoselectively as shown in FIG. 5, producing a substituted β-hydroxydiester with 2 chiral centers. Preferably, the reaction catalyzed by the ketoreductase is substantially diastereoselective. As used herein, the term "substantially diastereoselective" means a reaction that produces a compound containing two or more chiral centers with the product mixture containing at least about 50% of a single diastereomer of the possible diastereoisomers, preferably at least about 75% of a single diastereomer, and more preferably at least about 90% of a single diastereomer. As a chiral synthesis rather than a resolution, yields up to 100% of theoretical can be achieved during the enzymatic reductions, with two chiral centers being introduced in a single step in a substantially diastereoselective manner. The diastereomeric hydroxy diesters can be further converted to α-hydroxy-β-amino acids and β-hydroxy-γ-amino acids by regioselective hydrolysis of only one of the two ester functional groups and conversion of the remaining ester or carboxylic acid to an amine by a stereospecific rearrangement reaction which preserves the asymmetry at both chiral centers.

In a particularly preferred embodiment, the β-ketodiester is a compound having the following formula:

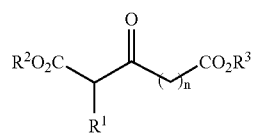

wherein n is 0 or 1, and $R^1$, $R^2$, and $R^3$ are each independently selected is selected from the group consisting of alkyl, substituted alkyl, aryl, substituted aryl, aralkyl, substituted aralkyl, heterocyclic, and substituted heterocyclic.

As used herein, the term "alkyl," alone or in combination, means a straight-chain or branched-chain hydrocarbon, either saturated or unsaturated, containing from 1 to about 12 carbon atoms. "Substituted alkyl" means alkyl groups substituted on one or more carbon atoms with one or more substituents selected from the group consisting of hydroxy, alkoxy, thio, thioalkyl, fluoro, chloro, bromo, iodo, carboxy, carboxyalkyl, carbamoyl, carbamide, amino, amidino, phosphate, phosphonate, phosphinate, phosphinyl, their derivatives, and the like.

As used herein, the term "aryl," alone or in combination, means a carbocyclic aromatic system containing from 1 to 4 rings, wherein said rings may be attached in a pendant manner to each other or may be fused to each other. Examples of aryl groups include phenyl, naphthyl, biphenyl, anthracenyl, and the like. Substituted aryl means aryl groups substituted on one or more carbon atoms with one or more substituents selected from the group consisting of hydroxy, alkoxy, thio, thioalkyl, fluoro, chloro, bromo, iodo, carboxy, carboxyalkyl, carbamoyl, carbamide, amino, arnidino, phosphate, phosphonate, phosphinate, phosphinyl, their derivatives, and the like.

As used herein, the term "aralkyl" means an alkyl group as defined above substituted with an aryl group as defined above. Substituted aralkyl means aralkyl groups substituted on one or more carbon atoms with one or more substituents selected from the group consisting of hydroxy, alkoxy, thio, thioalkyl, fluoro, chloro, bromo, iodo, carboxy, carboxyalkyl, carbamoyl, carbamide, amino, amidino, phosphate, phosphonate, phosphinate, phosphinyl, their derivatives, and the like.

As used herein, the term "heterocyclic," alone or in combination, means a saturated or unsaturated monocyclic or multi-cyclic group containing one or more heteroatoms selected from the group consisting of oxygen, nitrogen, sulfur, phosphorous, selenium, and silicon. Substituted heterocyclic means heterocyclic groups substituted on one or more carbon atoms with one or more substituents selected from the group consisting of hydroxy, alkoxy, thio, thioalkyl, fluoro, chloro, bromo, iodo, carboxy, carboxyalkyl, carbamoyl, carbamide, amino, amidino, phosphate, phosphonate, phosphinate, phosphinyl, their derivatives, and the like.

Some ketoreductase enzymes particularly useful in the present invention require the presence of nicotinamide cofactors in order to catalyze the reduction of the subject β-ketodiesters. As used herein, the term "nicotinamide cofactors" includes NAD+, NADH, NADP+, NADPH, and any derivatives thereof that can be used as cofactors by oxidoreductase enzymes. Nicotinamide cofactors useful in the present invention are readily available commercially from vendors, including Sigma-Aldrich Chemical Company (St. Louis, Mo. USA), BioCatalytics, Inc., (Pasadena, Calif. USA), Roche Diagnostics (Indianapolis, Ind. USA) and others well known to those skilled in the art. Derivatives of nicotinamide cofactors useful in the practice of this invention include the nicotinamide analogs reported in U.S. Pat. No. 5,801,006, the disclosure of which is hereby incorporated by reference, polyethyleneglycol functionalized nicotinamide molecules such as reported by Okada and Urabe in Methods in Enzymology, 136, 34–45 (1987), and the like. The concentration of nicotinamide cofactor used in the reaction mixture with a ketoreductase enzyme preferably ranges from about 0.001 mM to about 10 mM, and more preferably from about 0.01 mM to about 0.5 mM. For the stereoselective reduction to be carried out as described in the present invention, the reduced form of the nicotinamide cofactor (NADH, NADPH or analog thereof) is used by the ketoreductase enzyme. It is also possible to start with an oxidized form of the nicotinamide cofactor (NAD+, NADP+, or analog thereof), which is less expensive that the reduced form, provided that a source of reducing equivalents is furnished to reduce the oxidized form of said cofactor to the reduced form for the enzyme-catalyzed reduction to proceed.

In the method of the present invention, the nicotinamide cofactors can be recycled, if desired. Cofactor recycling can be achieved in cell-free enzymatic reactions by the use of an appropriate recycling enzyme in combination with a ketoreductase. Enzymes useful for the recycling of nicotinamide cofactors are well-known in the art, and include formate dehydrogenases, glucose dehydrogenases, sorbitol dehydrogenases, alcohol dehydrogenases and the like. Any of the recycling methods known in the art may be used in the practice of this invention. Some examples of cofactor recycling methods are described in *Preparative Biotransformations* (S. M. Roberts, editor), 3.1.1–3.1.6, John Wiley & Sons, Chichester, U.K. (1996) and references therein; Z. Shaked and G. M. Whitesides, *J. Am. Chem. Soc.* 102, 7104–5 (1980) and references therein; J. B. Jones and T. Takamura, Can. *J. Chem.* 62, 77 (1984); all hereby incorporated by reference.

In the practice of this invention, cofactor recycling may also be achieved by the use of a microorganism into which the genes encoding both the ketoreductase and the recycling enzyme have been cloned and expressed together. In this embodiment, the whole cell may be used as the catalyst, or, if desired, the ketoreductase and the recycling enzymes may be isolated from the cell. As used herein with respect to enzymes, the term "isolated" means extracted from or separated from cells. An isolated enzyme or enzymes may be used as a crude cell lysate, partially purified enzyme preparation, or a purified enzyme preparation.

In accordance with this invention, the ketoreductase and the recycling enzyme may be used as soluble enzymes or, if desired, one or both enzymes may be immobilized prior to use. When used as soluble enzymes, ketoreductases and recycling enzymes useful in the practice of this invention may be isolated from cells capable of producing the desired enzymes and used without purification, or purified partially or completely. The purification of the enzymes may be accomplished by techniques well known to those skilled in the art. Some examples of purification methods for enzymes are described in *Methods in Enzymology*, 22 (1971) and references therein, hereby incorporated by reference.

If the ketoreductase and the recycling enzymes are to be immobilized, techniques well known in the art can be used. Either the ketoreductase enzyme or the cofactor recycling enzyme may be immobilized separately, or both enzymes may be immobilized together. Such immobilization of the enzymes can be carried out by co-immobilization of both enzymes together on the same support material, or the ketoreductase and the recycling enzyme may be immobilized separately and the two immobilized enzymes can be combined in appropriate amounts for carrying out the diastereoselective reduction reaction. The appropriate amounts of immobilized enzymes to be used can be readily determined by persons skilled in the art. Methods for the immobilization of enzymes are well known to those skilled in the art. One example of an immobilized enzyme method useful in the practice of this invention is described by Weetall et al., *Methods in Enzymology* 34, 59–72 (1974), which is hereby incorporated by reference. In this method, enzymes may be immobilized on an amine-functionalized porous glass or ceramic support which has been activated with glutaraldehyde. It is also possible that whole cells containing the ketoreductase enzyme or both the ketoreductase enzyme and a recycling system may be immobilized, if desired, in the practice of this invention. Various exemplary methods for immobilization of both whole cells and enzymes which may be used in the practice of this invention are described in *Methods in Enzymology* 44 (1976), K. Mosbach editor, *Immobilization of Enzymes and Cells*, Gordon F. Bickerstaff, ed., Humana Press, Totowa, N.J. (1997) and in *Biocatalytic Production of Amino Acids and Derivatives*, D. Rozzell and F. Wagner, Eds., Hanser Publishers, Munich, (1992) pp. 279–319, all hereby incorporated by reference. It is understood that other similar methods exist and may also be used in the practice of this invention.

In the next step of the method of this invention, the substituted β-hydroxydiester, which is the immediate product of the diasereoselective reduction of the substituted β-ketodiester, is hydrolyzed regioselectively to the mono-carboxylic acid (FIG. 6).

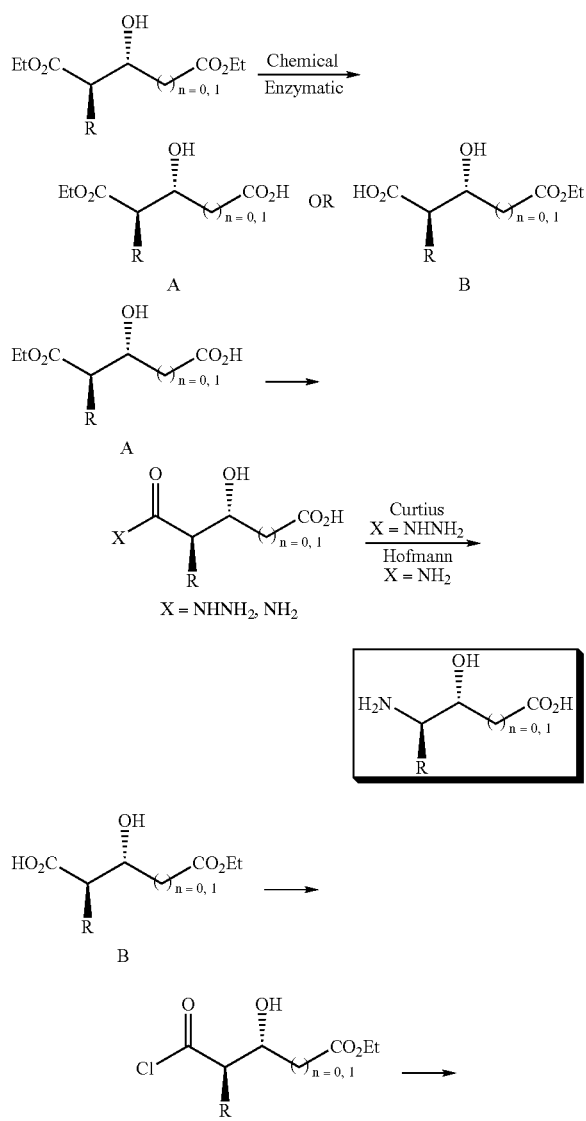

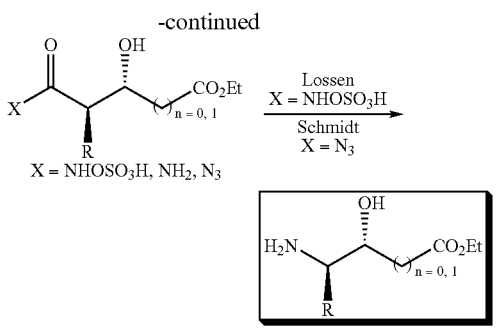

Figure 6. Regioselective chemical or enzymatic hydrolysis followed by rearr

As used herein, the term "hydrolyzed regioselectively" refers to the conversion of only one of the two ester groups (either the ester adjacent to the R-group or the ester 2 carbons removed from the R-group) as shown in the structure in FIG. 6 to the substantial exclusion of the other. As it relates to hydrolyzing regioselectively an ester in a molecule containing two or more ester groups, the term "substantial exclusion" means converting at least about 80%, preferably at least about 90%, and more preferably at least about 95% of one ester group while converting less than about 20%, preferably less than about 10%, and more preferably less than about 5% of any other ester group in the molecule. As long as only one of the two ester functional groups is hydrolyzed regioselectively to the substantial exclusion of the other, regardless of which one is hydrolyzed, the two carboxylate groups become chemically distinguishable as the non-hydrolyzed ester and the carboxylic acid.

Regioselective hydrolysis can be achieved enzymatically using a hydrolytic enzyme. Any hydrolytic enzyme capable of regioselective hydrolysis of the substituted β-hydroxydiester to the mono-carboxylic acid may be used. Suitable enzymes for this regioselective hydrolysis include proteases, amidases, lipases, esterases and the like. Many broad range lipases, proteases, and esterases are known that can hydrolyze esters with high regioselectivity. Suitable enzymes for regioselective hydrolysis of a given substituted β-hydroxydiester in accordance with the invention can be identified by routine screening of various hydrolytic enzymes. Examples of such hydrolytic enzymes can be found in the Chirazyme Screening Set or the ICR Screening Set, both available from BioCatalytics Inc. (Pasadena, Calif. USA). In a typical screening experiment, individual reaction mixtures are set up with each of the candidate hydrolytic enzymes and the target substituted β-hydroxydiester to be regioselectively hydrolyzed, and the progress of the reaction is monitored by any convenient assay method. Such assay methods include, but are not limited to, gas chromatography, thin-layer chromatography, high performance liquid chromatography, and the like. It is well known by persons skilled in the art how to identify and select a suitable hydrolytic enzyme for regioselective hydrolysis.

Alternatively, regioselective hydrolysis of the substituted β-hydroxydiester can be accomplished chemically by using an appropriate base under reaction conditions permitting the regioselective hydrolysis of only one of the two ester functional groups to the substnatial exclusion of the other. Such regioselective hydrolysis can be achieved using a variety of different bases, including, but not limited to, mineral bases such as sodium hydroxide, potassium hydroxide, calcium hydroxide, barium hydroxide, sodium carbonate, potassium carbonate, and calcium carbonate. Ammonium hydroxide may also be used. Other bases that may be used for regioselective hydrolysis in the practice of this invention include tertiary amine bases such as triethylamine, trimethylamine, tributylamine, tribenzylamine, and the like. The regioselective hydrolysis may be carried out in an aqueous reaction medium, in an aqueous reaction medium containing various amounts of added organic solvent, or in an organic medium containing only small amounts of water. The reaction medium may also be an aqueous/organic two-phase system, if desired. Determination of appropriate conditions for achieving regioselective mono-hydrolysis can be accomplished by routine experimentation by those skilled in the art. It the practice of this invention, it has been found that too high a molar ratio of base:substituted B-hydroxydiester results in over-hydrolysis (that is, hydrolysis of both of one ester functional groups, or at least some of the second ester functional group); whereas too low a molar ratio of base:substituted β-hydroxydiester results in residual amounts of unhydrolyzed diester. For achieving regioselective mono-hydrolysis of the substituted β-hydroxydiester, the preferred molar ratio of base:substituted β-hydroxydiester ranges from about 1:1 to about 1.5:1. The preferred temperature range for the hydrolysis reaction is from about 4° C. to about 100° C., and more preferably from about 20° C. to about 50° C. Although aqueous reaction conditions are typically employed for the regioselective mono-hydrolysis of the substituted β-hydroxydiester, co-solvents may be used, if desired, to improve the solubility of the diester or to modulate the rate of the reaction. Suitable co-solvents include ethanol, methanol, isopropanol, tetrahydrofuran, dioxane, dimethylsulfoxide, dimethyl formamide, and the like.

Following the regioselective mono-hydrolysis of the substituted β-hydroxydiester, either the carboxylic acid or the ester functional group is converted to an amine, or derivative thereof, by means of a stereospecific chemical rearrangement. The rearrangement reactions that can be used in the practice of this invention include the Curtius rearrangement and modified versions of the Curtius rearrangement, the Lossen rearrangement and the Hoffiann rearrangement (FIG. 6). These rearrangement reactions are well-studied reactions that are well known to those skilled in the art.

In one embodiment, the carboxylic acid is converted to an amine, or derivative thereof, by means of the Curtius-type rearrangement using the reagent diphenylphosphoryl azide (DPPA). Heating of the mono-carboxylic acid, produced by regioselective mono-hydrolysis of the substituted β-hydroxydiester, with DPPA in the presence of stoichiometric amounts of triethyl amine (TEA) in toluene gives in one step the aminoalcohol rearrangement product as the cyclic carbamate (urethane) derivative (FIG. 7).

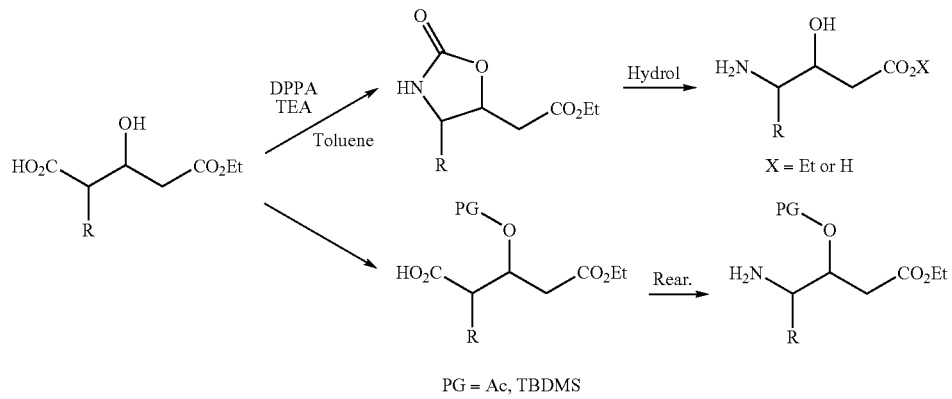

PG = Ac, TBDMS

Figure 7: Rearrangement of the acid with diphoshorylazide and triethyl amine gives a cyclic carbamate as the only product regardless of the presence or absence of alcohol in the reaction mixture. Protection of the alcohol first gives the free amine.

Formation of the mono acid to the corresponding acid azide after treatment with oxalyl chloride and sodium azide, and rearrangement by heating of the azide in tert-butanol or ethanol gave the cyclic carbamate (FIG. 7) as the major product. Small amounts of the ethyl carbamate can be observed when the reaction is carried out in ethanol. The urethane derivatives can be further converted to the corresponding amines, if desired, by hydrolysis under either acidic or basic conditions. The hydroxy group may be protected, if desired, prior to rearrangement. Typical protecting groups include, but are not limited to, simple esters such as acetyl, butyryl, benzoyl, phenylacetyl, and the like; ethers such as methyl ethoxymethyl, dihydropyranyl, and the like; silyl ethers such as t-butyl dimethyl silyl, trimethyl silyl, and the like; and carbonate esters such as t-butyloxy-carbonyl, carbobenzyloxy, and the like.

In another embodiment of this invention, the non-hydrolyzed ester functional group is converted to an amine. This conversion is accomplished in two steps. First, the ester is reacted with ammonia, hydrazine, or hydroxylamine to form the corresponding carboxamide, hydrazide, or hydroxamic acid, respectively. Then, the carboxamide, hydrazide, or hydroxamic acid is subjected to conditions permitting the stereospecific rearrangement to form the amine, or a derivative thereof. In each case, the rearrangement proceeds with retention of configuration of the migrating atom, and as a result, the optical purity of the final product is dependent on the stereoselectivity of the enzymatic reduction.

The stereospecific rearrangement may be carried out on the carboxamide via the Hofmann-type rearrangement [E. S. Wallis and J. F. Lane, *Organic Reactions* III, 267 (1949) and references therein; P. A. S. Smith, *Trans. N.Y. Acad. Sci.* 31, 504 (1969) and references therein; S. Simons, *J. Org Chem.* 38, 414 91973) and references therein; W. L. F. Armarego et al, *J. Chem. Soc. Perkin Trans.* I, 2229 (1976) and references therein; all hereby incorporated by reference]; on the hydroxamic acid via the Lossen rearrangement [S. Bittner et al (*Tet. Lett.* 23, 1965–8 (1974) and references therein; L.

Bauer and O. Exner, *Angew. Chem. Int. Ed.* 13, 376 (1974) and references therein; all hereby incorporated by reference]; or on the hydrazide via the Curtius rearrangement [Yamada, S. *Chem. Pharm. Bull.* 22, 1398 (1974); P. A. S. Smith, *Organic Reactions* III, 337 (1946) and references therein; J. H. Saunders and R. J. Slocombe, *Chem. Rev.* 43, 205 (1948) and references therein; D. V. Banthorpe in *The Chemistry of the Azido Group*, S. Patai Ed., Interscience, New York, 1971, pp. 397–405 and references therein; J. D. Warren and J. D. Press, *Synth. Comm.* 10, 107 (1980) and references therein; all hereby incorporated by reference].

The invention will now be further described by the following examples, which are presented here for illustrative purposes only and are not intended to limit the scope of the invention.

EXAMPLES

Example 1

Synthesis of 2-benzyl-3-ketoglutarate diethyl ester

To 100 mL of dry acetone was added diethyl 1,3 acetone dicarboxylate (20 mL, 0.11 mole), benzyl bromide (8 mL, 0.067 mole) and potassium carbonate (18 grams, 0.13 mole). The heterogeneous mixture was refluxed overnight with vigorous stirring. After 16 hours the reaction progress was checked by thin layer chromatography. All the benzyl bromide starting material had been consumed and an intense spot corresponding to the product 2-benzyl-3-ketoglutarate diethyl ester was observed. The solution was filtered, and the solids were washed with another 100 mL of acetone. The combined organic solutions were evaporated to dryness, leaving a yellow liquid. After silica gel chromatography using ethyl acetate/hexane (2/8, v/v) as the elution solvent, the product was obtained as a colorless liquid (17.4 grams, 89% yield). The actual yield towards the formnation of 2-benzyl-3-ketoglutarate diethyl ester was lower than 89% since a byproduct (probably the benzyl ether forming from oxygen substitution) coelutes from the silica column along with the 2-benzyl substituted product. For an alternative synthetic method, see Example 7.

Example 2

Synthesis of 2-methyl-3-ketglutarate diethyl ester

To 20 mL of dry tetrahydrofuran that had been purged with nitrogen was added 5 mL of diethyl 1,3 acetone dicarboxylate (27 millimole), and the solution was cooled to −15 C prior to the dropwise addition of 15 mL of 2 M lithium diisopropyl amide (30 millimole). The reaction mixture was maintained under a nitrogen atmosphere at −15 C, and 3 mL (48 millimole) of iodomethane were added slowly to the reaction mixture. The reaction was allowed to reach room temperature gradually over approximately 2.5 hours, and stirring was continued overnight. After 16 hours, the reaction mixture was poured into 150 mL of a 1:1 mixture of 0.1 N aqueous HCl and diethyl ether. The organic and aqueous layers were separated, the aqueous layer was extracted two more times with diethyl ether, and the combined organic extracts were back extracted with brine, dried over anhydrous $Na_2SO_4$ and evaporated to dryness. A yellow liquid was obtained which on gas chromatographic analysis showed a composition consisting of 47% 2-methyl-3-ketoglutarate di ethyl ester and 20% of the disubstituted product 2,4-dimethyl-3-ketoglutarate diethyl ester. After purification by silica gel chromatography using ethyl acetate/hexane (2/8, v/v) as the elution solvent, 1.5 grams of purified 2-methyl-3-ketoglutarate diethyl ester was obtained as a colorless liquid. The isolated yield was 30%.

Example 3

Synthesis of 2-isobutyl-3-ketoglutarate diethyl ester

Isobutyl iodide (2.5 mL, 14 millimole), diethyl-1,3-acetone dicarboxylate (2.5 mL 14 millimole) and powdered $K_2CO_3$ (2.5 grams, 18 millimole) were combined in 15 mL of dry acetone, and the heterogeneous mixture was refluxed overnight. After 16 hours, the reaction mixture was filtered through diatomaceous earth (Celite), the solids were washed with another 30 mL of dry acetone, and the combined organic solutions were evaporated to dryness. The product 2-isobutyl-3-ketoglutarate diethyl ester was further purified bv silica gel chromatography (ethyl acetate/hexane, v/v, 2/8), providing 2-isobutyl-3-ketoglutarate diethyl ester as a colorless oil (1 gram, 40% isolated yield).

Example 4

Screening of Enzymes to Determine the Best Ketoreductase for Reduction of 2-methyl-3-ketoglutarate diethyl ester The Ketoreductase Screening Set (KRED-8000; BioCatalytics, Inc., Pasadena, Calif. USA) containing eight different ketoreductases was screened to determine the best enzyme for the diastereoseelctive reduction of 2-methyl-3-ketoglutarate diethyl ester. Eight individual reaction mixtures were set up containing, in 1 mL of 300 mM potassium phosphate pH=6.5, the following components: 25 mM 2-methyl-3-ketoglutarate diethyl ester, 5 mM NADPH, 100 mM NaCl, 10% (v/v) glycerol, 200 mM glucose, 5% (v/v) DMSO, and 2 mg glucose dehydrogenase for NADPH recycling. To each reaction mixture was added 5 milligrams of a different lyophilized ketoreductase KRED 1001. All eight reactions were left at 37 C overnight. After 16 hours, each reaction mixture was extracted with ethyl acetate and the reaction products were analyzed using gas chromatography. The enzymes in the screen and the yield of reduction product obtained were as follows: KRED 1001, 97%; KRED 1008, 90%; KRED 1007, 55%; KRED 1004, 59%. The yield of reduction product was 10% or less for the other 4 KRED enzymes.

Example 5

Screening of Enzymes to Determine the Best Ketoreductase for Reduction of Other 2-substituted-β-ketodiesters The method of Example 4 was repeated except that 2-methyl-3-ketoglutarate diethyl ester was replaced with either 2-benzyl-3-ketoglutarate diethyl ester or 2-isobutyl-3-ketoglutarate diethyl ester. The best enzyme for the reduction of 2-benzyl-3-ketoglutarate diethyl ester was KRED 1008, and the best enzymes for the reduction of 2-isobutyl-3-ketoglutarate diethyl ester were KRED 1008 and KRED 1001.

Example 6

Chiral Analysis of the Diastereoselectivity of the Reduction of 2-Substituted-β-ketodiesters Analysis of the diastereoselectivity of the reduction of 2-substituted-β-ketodiester was performed. The enzymatic reduction products of 2-methyl-3-ketoglutarate, 2-benzyl-3-ketoglutarate, and 2-isobutyl-3-ketoglutarate were analyzed using chiral gas chromatography using a ChiralDex column (Chiral Technologies). For the 2-methyl-3-hydroxyglutarate diester, the analysis was carried out under isocratic conditions at 130 C. In the case of isobutyl and benzyl substituted compounds, successful separation of all four diastereomers was achieved after derivatizing the reduction products as the corresponding acetate esters by reaction with acetic anhydride and using a temperature gradient. A typical protocol for the preparation of these compounds in small scale was as follows: a sample (5–10 mg) of alcohol was dissolved in 0.5 mL diethyl ether, and 1 drop of triethylamine, 20 μL of acetic anhydride and a catalytic amount 4-dimethyl aminopyridine were added. The mixture was left in a tightly closed vial for 4–16 hours, and then it was extracted with 1 mL of aqueous HCl (1 N) and 1 mL of a $Na_2CO_3$ (1 N) solution. The products were analyzed by gas chromatography. A temperature gradient was used for elution. For the benzyl derivative the conditions were as follows: 2 minutes at 175 C, increase in temperature by 1.5 C /minute to 200 C, and then remaining for 10 minutes at 200 C. For the isobutyl-substituted compound the conditions were as follows: 2 minutes at 165 C, and increase in temperature by 1.5 C /minute to 190 C. Baseline separation of all four diastereomers was achieved under these conditions and the product ratios were calculated. For the 2-methyl substituted diester, KRED 1008 produced a single diastereomer as 91% of the product mixture, KRED 1007 produced a single diastereomer as 89% of the product mixture, KRED 1004 produced a single diastereomer as 84% of the product mixture, and KRED 1001 produced a single diastereomer as 65%. In the case of the 2-benzyl substituted diester, KRED 1008 produced a single diastereomer as 100% of the product mixture; no other diastereomers were detected. In the case of the 2-isobutyl substituted diester, KRED 1001 produced a single diastereomer as 94% to 97% of the product mixture.

Example 7

Alternate synthesis of diethyl 2-benzyl 3-ketoglutarate and reduction with 1008

In 60 mL of tetrahydrofuran (THF) 15 mL of 1,3 acetone dicarboxylate (0.072 mole) were dissolved. Under nitrogen atmosphere the mixture was cooled at −18 C for 10 minutes before 74 mL (0.148 mole) of lithium diisopropylamine (LDA) solution (2M in hexane) was slowly added over a period of 20 minutes. After stirring the solution at −18 C for 10 minutes, 10 mL of tertahydrofuran mixed with 9.5 mL of benzyl bromide (0.080 mole) were slowly added, and the solution was stirred for another 2.5 h (temperature was slowly increased to −10 C ) before complete reaction was observed by thin layer chromatography analysis of reaction aliquots. The reaction mixture was then poured into 100 mL of an aqueous solution containing 2M hydrochloric acid and 200 mL of ethyl acetate. The aqueous layer was extracted one more time with 100 mL of ethyl acetate, and the combined organic layers were extracted once with 50 mL of brine. After drying of the organic layer with sodium sulfate, solvent evaporation gave 25 g of an oily product that was incubated with enzyme 1008 without any further purification according to the following reaction conditions: In 250 mL of water containing 200 mM of potassium phosphate (pH 6.8) 2.5% (v/v) dimethyl sulfoxide, 0.2 M of sodium chloride, 5 g of D-glucose, 0.1 g of NADP+ and 100 mg of lyophilized glucose dehydrogenase and KRED 1008, 3.3 g of crude 2-benzyl 3-ketoglutarate were added. The reaction was incubated in a shake oven at 37 C for 12 h before another batch of NADP+ (0.1 g), KRED 1008 (0.1 g) and glucose dehydrogenase (0.1 g) were added to the reaction mixture. Incubation for 20 more hours gave complete conversion of the ketone to the alcohol as shown by high pressure liquid chromatography and thin layer chromatographic analysis of crude reaction extracts. The aqueous reaction mixture was then extracted with ethyl acetate (3×, 100 mL each) and the combined organic layers were washed with brine and dried with sodium sulfate. Solvent evaporation gave 3.2 g of an oily product from which 2.2 g of pure diethyl 2-benzyl 3-hydroxy glutarate were isolated after silica gell chromatographic purification. Based on the recovery of pure alcohol from the 3.3 g of crude diethyl 2-benzyl 3-ketoglutarate the overall yield to 2-benzyl 3-hydroxy glutarate as calculated from the starting 1,3 acetone dicarboxylate was 80%.

Example 8

Enzyme-catalyzed diastereoselective reduction of 2-methyl-3-ketoglutarate diethyl ester To 40 mL of 300 mM potassium phosphate buffer, pH=6.5, containing NaCl (100 mM), DMSO (3% v:v), glucose (200 mM), and glycerol (10% v:v), 40 mM of 2-methyl-3-ketoketoglutarate diethyl ester was added along with 100 mg of lyophilized KRED 1008 and 30 mg of glucose dehydrogenase. The reaction mixture was incubated for 48 hours at 37 C. Gas chromatographic analysis showed that the yield of hydroxy diester product was greater than 80%. The product was isolated by extraction of the reaction mixture with ethyl acetate and purification using silica gel chromatography. Isolated yield was in the range of 85–95%.

Example 9

Enzyme-catalyzed diastereoselective reduction of 2-isobutyl-3-ketoglutarate diethyl ester To 40 mL of 300 mM potassium phosphate buffer buffer, pH=6.5, containing NaCl (100 mM), DMSO (3% v:v), glucose (200 mM), and glycerol (10% v:v), 40 mM of 2-isobutyl-3-ketoketoglutarate diethyl ester was added along with 100 mg of lyophilized KRED 1001 and 30 mg of glucose dehydrogenase. The reaction mixture was incubated for 48 hours at 37 C. Gas chromatographic analysis showed that the yield of hydroxy diester product was greater than 80%. The product was isolated by extraction of the reaction mixture with ethyl acetate and purification using silica gel chromatography. Isolated yield was in the range of 85–95%.

Example 10

Reduction of 2-benzyl-3-ketoglutarate Diethyl Ester Using Whole Cells Expressing KRED 1008

Whole cell reductions of 2-benzyl-3-ketoglutarate were carried out using *E. coli* cells expressing the gene encoding KRED 1008. Cells were grown overnight at 30 C in 400 mL of a Luria Broth/glucose (2 g/L)/ampicillin (100 mg/L) media. The cells were isolated by centrifugation and resuspended in 400 mL of a minimal salt (M9) solution containing isopropylthiogalactoside (IPTG, 0.5 mM), glucose (5 g/L), ampicillin (100 mg/L), and 2-benzyl-3-ketoglutarate diethyl ester. In independent experiments, the concentration of 2-benzyl-3-ketoglutarate diethyl ester was varied over the range of 1 gram/liter to 7.5 grams/liter. Cells continued to grow at 30 C after addition of the ketodiester substrate. Samples were removed at regular time intervals and analyzed for product formation using gas chromatography until complete reaction was observed. Although the 2-benzyl-3-ketoglutarate diethyl ester substrate did not completely dissolve in the aqueous buffer, and although no DMSO co-solvent was used, the reduction reactions were complete after 20–40 hours. In reactions that were allowed to proceed for more that 24 hours, another portion of glucose (1–3 g) and IPTG (0.4 mL of a 0.5 M solution) were added. The product 2-benzyl-3-hydroxyglutarate diethyl ester was isolated by removal of the cells by centrifugation and extraction of the reaction mixture with ethyl acetate. The yield of 2-benzyl-3-hydroxyglutarate diethyl ester in all cases was greater than 80%.

Example 11

Reduction of other 2-substituted-3-ketoglutarate Diesters Using Whole Cells Expressing Ketoreductase Genes The procedure of Example 10 is repeated with E. coli cells expressing a ketoreductase gene appropriate for the reduction of the target 2-substituted-3-ketoglutarate diester. The product 2-substituted-3-hydroxyglutarate diesters are isolated by removal of the cells and extraction of the reaction mixtures with ethyl acetate.

Example 12

Synthesis of 3-benzyloxaloacetate diethyl ester

In 7 mL tetrahydrofuran 1 g (4.8 milimole) diethyl oxaloacetate sodium salt was dissolved. In 5 mL tertahydrofuran 0.7 mL of benzyl bromide (5.9 milimole) are dissolved and added to the previous mixture. The reaction was refluxed for 9 h before thin layer chromatography analysis showed consumption of all reactants. Product purification started by adding the reaction mixture in 40 mL aqueous solution containing 0.5 M HCl and 40 mL ethyl acetate. The water layer was extracted one more time with ethyl acetate and the combined organic solvents were back extracted with brine, dryied with sodium sulfate and evaporated to dryness. After silica gel chromatography 0.25 g (19% yield) of pure 3-benzyloxaloacetate diethyl ester were isolated.

Example 13

Alternative synthesis of 3-benzyloxaloacetate diethyl ester 1 mL (5.6 milimole) of ethyl hydroxyccinamate was dissolved in 10 mL of tetrahydrofuran, and the solution was cooled at −15 C before 2.9 mL (7.3 milimole) of butyl lithium (2.5 M solution in hexanes) was slowly added. After stirring the reaction for 10 min at −15 C, 0.8 mL (8.4 milimole) of diethyl oxalate were added, and the reaction was left slowly to reach room temperature (about 2 hours). After stirring at room temperature overnight, the mixture was mixed with 70 mL of water (containing 0.1 M HCl) and extracted twice with diethyl ether. Combined organic extracts were back extracted with brine, dryed with sodium sulfate and evaporated to dryness. Pure 3-benzyloxaloacetate diethyl ester (0.8 g, 51% yield) was obtained after silica gel chromatographic purification of the crude oily reaction product.

Example 14

Enzyme-catalyzed diastereoselective reduction of 3-benzyloxaloacetate diethyl ester The procedure of Example 4 was repeated for the screening of the KRED-8000 kit with 3-benzyloxaloacetate diethyl ester. Enzymes KRED 1008 and KRED 1004 showed complete reduction to the alcohol. Both reactions were repeated in larger scale for the purpose of isolating the product and verifying the structure using 1H NMR spectroscopy. In 20 mL of an aqueous solution containing 250 mM potassium phosphate (pH 6.7), 5% (v/v) polyethelene glycol (MW 1450) 0.5 M sodium chloride, 0.076 g of NADP+, 3.5 g of D-glucose 0.1 g of both lyophilized enzymes glucose dehydrogenase and KRED 1004 or KRED 1008 0.5 g of 3-benzyloxaloacetate diethyl ester were added. The reactions were incubated at 37 C in a shake oven for 20 h before they were extracted with ethyl acetate. The organic layers were evaporated to dryness, and the alcohols were further purified using silica gel chromatography, before they were analyzed by $^1$H NMR. Both enzymes gave 2-hydroxy-3-benzylsuccinate diethyl ester as the only product.

Example 15

Chiral analysis of enzymaticaly-produced 3-substituted oxaloacetate diesters

For the determination of the stereochemistry of the ethyl 3-benzyl 2-hydroxy succinate, standard compounds with known stereochemistry were chemically synthesized according to published literature procedure (Org. Synth, Vol 63, pg 109). The two enantiomeric ethyl 3-benzyl 2-hydroxy succinates were separated using chiral HPLC chromatography (Column: CHIRALCEL OD-RH, eluent: $H_2O$/MeOH, v/v, 70/30 flow rate: 1 mL/min). Analysis of the reaction product of diethyl-2-benzyl oxoglutarate and KRED 1008 showed only one peak that co-eluted with (2R, 3S) 3-benzyl 2-hydroxysuccinate. KRED 1004, on the other hand, gave (2S, 3R) 3-benzyl 2-hydroxysuccinate as the major product (62%) along with smaller amounts (14%) of the (2R, 3S) and another peak (24%) that is either the (2S, 3S) or (2R, 3R) diastereomer.

Example 16

Enzyme-catalyzed diastereoselective reduction of various 2-substituted-3-ketoglutarate and 3-substituted oxaloacetate diesters It is appreciated that using procedures analogous to those described in previous Examples 1 to 15 the reduction of a wide range of different various 2-substituted-3-ketoglutarate and 3-substituted oxaloacetate diesters can be produced. Using a screen such as that described in Example 4, the best enzyme for the diastereoselective reduction can be identified, and the reaction can be carried out at a preparative scale as described in Examples 6 to 11. Diastereoselective reduction of the following representative compounds is envisioned: 2-isobutyl-3-ketoglutarate dimethyl ester, 2-methyl-3-ketoglutarate dimethyl ester, 2-benzyl-3-ketoglutarate dimethyl ester, 2-phenyl-3-ketoglutarate diethyl ester, 2-allyl-3-ketoglutarate diethyl ester, 2-propargyl-3-ketoglutarate diethyl ester, 2-(4-pyridyl)-3-ketoglutarate diethyl ester, 2-isopropyl-3-ketoglutarate diethyl ester, 2-propyl-3-ketoglutarate diethyl ester, 2-isopentyl-3-ketoglutarate diethyl ester, 2-(2-thienyl)-3-ketoglutarate diethyl ester, 3-isobutyloxaloacetate dimethyl ester, 3-methyloxaloacetate dimethyl ester, 3-benzylyloxaloacetate dimethyl ester, 3-phenylyloxaloacetate diethyl ester, 3-isopentyloxaloacetate diethyl ester, 3-propyloxaloacetate diethyl ester, 3-allyloxaloacetate diethyl ester, 3-propargyloxaloacetate diethyl ester, 3-(4-pyridyl)oxaloacetate diethyl ester, and 3-(2-thienyl)oxaloacetate diethyl ester.

Example 17

Screening to Find a Hydrolytic Enzyme Capable of Catalyzing the Regioselective Hydrolysis of 2-benzyl 3-hydroxy-diethyl ketoglutarate A Chirazyme Screening Set (BioCatalytics, Inc., Pasadena, Calif.) was used to screen for a hydrolytic enzyme capable of catalyzing the regioselective hydrolysis of 2-benzyl-3-hydroxy-diethyl ketoglutarate, produced by stereoselective reduction as in Example 7. Each of the 11 hydrolytic enzymes in the Chirazyme Screening Set (1 mg) was incubated at 37 C in a potassium phosphate buffer solution (250 mM, pH=7; 1 mL total volume) containing 40 mM of 2-benzyl 3-hydroxy-diethyl ketoglutarate and 5% (v/v) DMSO. The reaction progress was analyzed at 2 h and 24 h using high performance liquid chromatography after each sample was acidified to pH 1–2 by the addition of HCl and extracted with ethyl acetate. Enzymes L2, L3, L8, L9 and E1 gave product. As shown in Table 1, all enzymes gave initially the mono-acid hydrolysis product of 2-benzyl 3-hydroxy-diethyl ketoglutarate, which in most cases was further hydrolyzed to produce the di-acid in significant yields, with the exception of L9, which gave minor diacid product even after 24 h of incubation with the substrate. Although the mono-acid product that was obtained in all these reactions had the same retention time in HPLC analysis, the reactions with L2, L3, L9 and E1 were scaled up (10 mL solution, 80 μL substrate, 10 mg enzyme), and allowed to react for 4–10 h until only the mono-acid was formed. Product was isolated after extracting the reaction mixture with EtOAc at neutral pH to remove any unreacted ester, followed by extraction at acidic pH, which removed all the acids from the water. $^1$H NMR analysis of all 4 reactions identified the product to be the same less hindered mono-acid A (FIG. 6). In support of this conclusion, literature precedent predicts that the less hindered ester group of 2-benzyl-3-hydroxy diethyl glutarate will react more rapidly in the presence of a hydrolytic enzyme (K Faber, Biotransformations in Organic Chemistry, 3$^{rd}$ edition, Chapter 2, Springer Verlag, Berlin-Heidelberg-New York, 1997). Additional proof of the structure of the mono-acid was obtained after the L2- and chemical- (Example 18) hydrolyzed diethyl 2-benzyl 3-hydroxy glutarate was rearranged with DPPA to the corresponding primary cyclic carbamate (FIG. 7) and analyzed by $^1$H NMR spectroscopy. Details for this reaction are presented in Examples 24 and 25.

TABLE 1

Enzymatic hydrolysis of diastereoselectively-reduced 2-benzyl-3-ketoglutarate diester.

| Enzyme | Time (h) | SM % | Mono-acid | Di-acid |
|---|---|---|---|---|
| L2 | 2 h | 38 | 62 | — |
|    | 24 h | — | 64 | 36 |
| L3 | 2 h | 70 | 30 | — |
|    | 24 h | — | 58 | 42 |
| L8 | 2 h | 100 | — | — |
|    | 24 h | 78 | 22 | — |
| L9 | 2 h | 48 | 52 | |
|    | 24 h | — | 91 | 9 |
| E1 | 2 h | 6 | 94 | — |
|    | 24 h | — | 50 | 50 |

Example 18

Regioselective Chemical Hydrolysis of 2-benzyl 3-hydroxy-diethyl ketoglutarate

Mild chemical hydrolysis reaction conditions were tested for the hydrolysis of 2-benzyl-3-hydroxy diethyl glutarate coming from the reduction with KRED 1008 as in Example 7. In small-scale reactions (1.5 mL total volume) various basic hydrolysis conditions (different solvents and ratios as well as NaOH concentrations) were prepared and the reaction progress was followed using HPLC analysis. Every sample that was analyzed was first acidified with glacial acetic acid and injected without any other treatment onto a C18 reverse phase column. Table 2 shows the two best reaction conditions found for the hydrolysis of 2-benzyl-3-hydroxy diethyl glutarate. Incubating the hydroxydiester in a mixture of Ethanol/H$_2$O (v/v, 2/8) containing differing amounts of NaOH and analyzing the reaction progress with HPLC showed the formation of two products. The compound with the longer retention time formed quickly, even under very mild hydrolysis conditions. Isolation and $^1$H NMR analysis of this compound showed it to be a monoester, identical to that obtained from the reactions with the regioselective hydrolysis catalyzed by the hydrolytic enzyme in Example 17.

TABLE 2

Hydrolysis of KRED 1008-reduced 2-benzyl-3-ketoglutarate

| | Conditions A$^a$ | | | Conditions B$^b$ | | |
|---|---|---|---|---|---|---|
| Time | SM | Mono-acid | Di-acid | SM | Mono-acid | Di-acid |
| 0.0$^c$ h | 13% | 87% | | 87% | 13% | |
| 0.5 h | | 75% | 25% | 8% | 92% | |
| 1.5 h | | 52% | 48% | | | |

$^a$Conditions A: H$_2$O/EtOH (v/v, 8/2) 0.05M substrate, 0.25 M NaOH incubate at RT.
$^b$Conditions B: H$_2$O/EtOH (v/v, 8/2) 0.05M substrate, 0.075 M NaOH incubate at RT.
$^c$This time point was taken immediately after the mixing of substrate and the NaOH solution.

The possibility of isomerization of either of the two chiral centers of the alcohols under the hydrolysis conditions was then evaluated. The monoacid product of the chemical hydrolysis under Conditions B was isolated, esterified with CH$_2$N$_2$, and analyzed by chiral gas chromatography. No new peaks were detected, thus indicating that no isomerization of either chiral center occurred under the chemical hydrolysis conditions employed.

Example 19

Whole Cell Reduction of 2-methyl 3-hydroxy Diethyl Glutarate and Enzymatic Hydrolysis After establishing that some of the lipases were able to hydrolyze the KRED 1008-reduced 2-benzyl 3-hydroxy diethyl glutarate, the same set of enzymes was tested for its ability to hydrolyze the KRED 1008-reduced 2-methyl 3-hydroxy diethyl glutarate. This compound was obtained after the whole cell reaction of 2-methyl diethyl 3-ketoglutarate using recombinant *E. coli* expressing KRED 1008 as described in Example 10. A mixture of diastereomers was obtained, and because the identify of the absolute stereochemistry of each one is currently unknown, they are indicated as A, B, C, and D in Table 3. From the retention times of each compound in the chiral GC, two sets of enantiomeric pairs were identified. Peaks A and B were assigned as representing on enantiomeric pair and peaks C and D were assigned as representing the other enantiomeric pair. Interestingly, the yield of the major diastereomer (indicated as C) in the whole-cell reactions dropped to ~75% from the 91% (Example 6) yield that was obtained in the cell-free reductions using lyophilized 1008. This was most likely due to the competing reductions of the starting material by native *E. coli* ketoreductases.

TABLE 3

Hydrolysis of KRED 1008-reduced 2-methyl 3-hydroxy diethyl glutarate

| Enzyme | Starting material | | Product | |
|---|---|---|---|---|
| | Yield % | Isomers (%) | Yield % | Isomers (%) |
| L2 | 0 | A&B (0) | >98 | A(17) B(6) |
| | | C&D (0) | | C(66) D(11) |
| L3 | 10 | A&B (50) | 90 | A(12) B (6) |
| | | C&D (50) | | C(77) D(5) |
| L5 | 80 | A&B (~0) | 20 | A(24) B(16) |
| | | C(>98)D (~0) | | C(18) D(42) |
| E1 | 0 | A&B (0) | >98 | A(15) B(6) |
| | | C&D (0) | | C(75) D(4) |

Enzymatic hydrolysis reactions were performed as follows: Solutions (2 ML) containing 300 mM potassium phosphate (pH=7), 2 mg enzyme and 30 mM of substrate were incubated at 37 C in a shake oven. As shown in Table 3 above, out of all 9 enzymes only L2, L3, L5 and E1 showed good product formation after 1.5 h of reaction at 37 C. Product identification was achieved as follows: after 1.5 h of incubation at 37 C each reaction was acidified to pH~1–2 with HCl (1N) addition and the solutions were extracted twice with ethyl acetate. The combined organic layers were evaporated to dryness, and the oily product was re-dissolved in diethyl ether and treated with an excess of $CH_2N_2$ before it was analyzed using chiral GC chromatography. Under the conditions employed for analysis, all four diastereomers of the 2-methyl 3-hydroxy methyl ethyl glutarate (coming from hydrolysis and reaction with $CH_2N_2$) and the four diastereomers of the starting material, 2-methyl 3-hydroxy diethyl glutarate, were clearly separable. Integration of these product mixtures gave the numbers presented in Table 3 above. Notice the reaction with L5 where the enzyme reacted more slowly with the major diastereomer, giving after 1.5 h of reaction a single diastereomer in as unreacted starting material in high yields. This example shows how the stereoselectivity of the hydrolytic enzyme can be a useful adjunct to the diastereoselective reduction. By selecting a hydrolytic enzyme (in this case, L5) that catalyzes the hydrolysis of the diastereomeric diesters at different rates, the diastereoselectivity of the monoacid or diester obtained can be improved. In this case, the diastereomer C of the diester is obtained as the only diastereomer after hydrolysis of the minor contaminating diastereomeric diesters.

Example 20

Chemical and Enzymatic Hydrolysis of 2-isobutyl 3-hydroxy Diethyl Glutarate

The mild hydrolysis conditions that were shown to give a single mono-ester product with 2-benzyl 3-hydroxy diethyl glutarate were utilized for the hydrolysis of the KRED 1001-reduced 2-isobutyl 3-hydroxy diethyl glutarate. Under these conditions, in 4 mL of $H_2O$/EtOH (8:2, v:v) containing 50 mM of NaOH, 25 mg (25 mM) of 2-isobutyl 3-hydroxy diethyl glutarate were added and the reaction was stirred for 1.5 h at room temperature. Product purification was achieved after acidification of the reaction mixture with HCl and extraction with EtOAc. Proton NMR analysis of the crude isolated product revealed the formation of a single mono-ester product, which was the outcome of the hydrolysis of the less hindered ester group A (FIG. 6).

Enzymatic methods using the previously utilized hydrolytic enzymes were also tested for hydrolysis of 2-isobutyl 3-hydroxy diethyl glutarate. Under these reaction conditions, 2 mL of a solution containing potassium phosphate buffer 300 mM (pH=7), 5% v/v DMSO, 2 mg of each enzyme and 10 μL of 2-isobutyl 3-hydroxy diethyl glutarate were incubated at 37 C in a shake oven. The reaction progress was monitored as follows: at specific time points samples (0.3 mL) from each reaction mixture were taken, acidified to pH ~2 with HCl (2N), extract with ethyl acetate (0.3 mL) and dried with $MgSO_4$. The organic layer was then evaporated to dryness, mixed with 0.4 mL of $Et_2O/CH_2N_2$ mixture to form the methyl ester and analyzed with GC chromatography (Chiral column, isocratic 170 C). All three diethyl, mono-ethyl-mono-methyl and di-methyl products were easily separated. Proof of the structure of the monoacid was obtained after the L2-hydrolyzed diethyl 2-isobutyl 3-hydroxy glutarate was rearranged with DPPA to the corresponding primary cyclic carbamate (FIG. 7) and analyzed by $^1H$ NMR spectroscopy. Details for this reaction are presented in Examples 24 and 25.

TABLE 4

Enzymatic hydrolysis using 2-isobutyl 3-hydroxy diethyl glutarate

| Enzyme | Time (h) | Mono acid | | Di-acid | | SM | |
|---|---|---|---|---|---|---|---|
| | | Yield | A/B[a] | Yield | A/B | Yield | A/B[a] |
| L2 | 2 h | 29% | 97/3 | | | 71% | 94/6 |
| | 24 h | 100% | 96/4 | | | | |
| L3 | 2 h | 100% | 94/6 | | | | |
| | 24 h | 100% | 94/6 | | | | |
| L9 | 2 h | | | | | | |
| | 24 h | 100% | 95/5 | | | | |
| E1 | 2 h | 100% | 96/4 | | | | |
| | 24 h | 86% | 93/7 | 14% | 100/0 | | |
| | 32 h | 47% | 90/10 | 53% | 97/3 | | |
| E2 | 2 h | 100% | 96/4 | | | | |
| | 24 h | 91% | 96/4 | 9% | 89/11 | | |
| | 32 h | 88% | 95/5 | 12% | 89/11 | | |

[a]Ratio of diastereomers.

As described in Example 6, two diastereomers (indicated as A and B in the above Table 4) in a ratio of 97% to 3% were formed from the enzymatic reduction of 2-isobutyl 3-keto diethyl glutarate and KRED 1001. As a result, the stereoselectivity of the enzymatic hydrolysis was also investigated. The previous methylated samples were evaporated to dryness and treated with a solution (0.3 mL) of $CH_2Cl_2$ that contained an excess of $Ac_2O$ and catalytic a amount of TMSOTf. Under these conditions the alcohols are acetylated and the diastereomers separate in Chiral GC (retention times: 19.1 min di-ethyl, 15.2 min mono-ethyl-mono-methyl; 12.5 min di-methyl; Chiral column; 145 C for 2 min then 145 to 180 C at 0.5 C/min). The ratio of diastereomers that was forming during the enzymatic hydrolysis is shown in the Table 4 above. The mono-acid that is formed in each reaction is the same and corresponds to the less hindered mono-acid A (FIG. 6). In the case of enzymes E1 and E2 further hydrolysis of the more hindered ester to the diacid was obtained when the reactions were incubated for longer times. In the case of E1, the two diastereomers were hydrolyzed at slightly different rates. This example further illustrates how stereoselective hydrolysis catalyzed by an enzyme can further improve the stereoisomeric purity of the mono-acid or diacid products.

Example 21

Chemical and enzymatic hydrolysis of 3-benzyl-2-hydroxysuccinate diethyl ester

Both mild chemical and enzymatic conditions were tested for the hydrolysis of 3-benzyl 2-hydroxysuccinate. (2S, 3R) 3-Benzyl 2-hydroxysuccinate (150 µL, 0.53 mmole) was incubated with a mixture of 2 mL of an aqueous NaOH (0.5 M) solution and 0.4 mL of ethanol. After stirring for 2 h at RT, acidification and extraction of the reaction mixture with EtOAc gave a single product, which was identified as either the mono-acid A or B (FIG. 6) using $_1$H NMR spectroscopy.

TABLE 5

Enzymatic hydrolysis of 3-benzyl 2-hydroxysuccinates

| Enzyme | Substrate | Time (h) | Mono-acid Yield (%) | Mono-acid A/B[a] | Starting material Yield (%) | Starting material A/B[a] |
|---|---|---|---|---|---|---|
| L6 | 2S, 3R | 4 h | 11 | 100/0 | 89 | 90/10 |
|  |  | 24 h | 46 | 100/0 | 54 | 85/15 |
|  | 2R, 3S | 4 h | 0 |  | 100 | 87/13 |
|  |  | 24 h | 7 |  | 92 | 87/13 |
| L7 | 2S, 3R | 4 h | 12 |  | 88 | 90/10 |
|  |  | 24 h | 53 | 100/0 | 47 | 82/17 |
|  | 2R, 3S | 4 h | 7 |  | 93 | 86/14 |
|  |  | 24 h | 30 | 81/19 | 68 | 85/15 |

[a]Ratio of diastereomers in reactant and product.

Enzymatic hydrolysis of both the (2S, 3R) and (2R, 3S) 3-benzyl 2-hydroxysuccinates was then investigated using the Chirazyme screening kit. Both these compounds were synthesized chemically according to literature procedures (Org. Synth. Vol 63, pg. 109) and both contained about 10–13% of a diastereomeric impurity, which was the (2S, 3S) for the synthesis of (2S, 3R) and the (2R, 3R) for the synthesis of (2R, 3S). Aqueous solutions (2 mL) containing 250 mM Kpi pH 7, 5% v/v DMSO 5 µmL of each enantiomer and 2 mg/mL of each lipase were incubated in a shake oven at 37 C. Samples were taken and analyzed using HPLC chromatography. Both enantiomers after 24 h of incubation were hydrolyzed to the mono-acid by lipase L2, L7 and E1, while L6 seems to react faster with the (2S, 3R) enantiomer. All hydrolysis reactions gave a single product, which had the same retention time (at HPLC analysis) with the $^1$H NMR-characterized product of the mild chemical hydrolysis. In a second experiment, hydrolysis reactions of (2S, 3R) and (2R, 3S) 3-benzyl 2-hydroxysuccinates using L6 and L7 under identical conditions (Kpi, 250 mM pH 7, 5% v/v DMSO, 2 mg/mL enzyme and 5 µL/mL diester) were performed and the reaction progress as well as the ratio of diastereomers in both the starting materials and the products were measured. As shown in Table 5 above, L6 hydrolyzed preferably the (2S, 3R) 3-benzyl 2-hydroxysuccinate isomer. The same selectivity for the hydrolysis of the (2S, 3R) isomer was also observed in the hydrolysis using L7. However, this enzyme also reacted with lower rates with the other diastereomers of 3-benzyl 2-hydroxysuccinate.

Example 22

Formation of the More Hindered mono-acid of 2-benzyl 3-hydroxy glutarate

Formation of the more hindered mono-acid B provides a useful precursor for rearrangement. (FIG. 6). This molecule was synthesized in a two-step hydrolysis-esterification process. Since the less hindered mono-acid A was preferably forming under mild hydrolysis conditions as well as in the reactions with certain commercially-available lipases, it was hypothesized that it would also be esterified much faster if the 2-benzyl 3-hydroxy glutarate diacid reacts with ethanol under mild conditions. As a result, incubating 2.1 grams (7.2 mmole) of 2-benzyl 3-hydroxy diethyl glutarate in 7 mL of a 5 M (35 mmole) KOH aqeuous solution also containing 1 mL EtOH at room temperature gave complete conversion to the diacid (I) (FIG. 7) after stirring for 3–4 h. The product was isolated (1.6 gr, 95% yield) after acidification of the reaction mixture with HCl and extraction with EtOAc. Selective esterification was achieved when diacid (I) was stirred in 25 mL of EtOH at 45 C for 18 hours in the presence of one drop of concentrated $H_2SO_4$. The reaction was followed by HPLC and only the mono-ester II (FIG. 7) was shown to form under the reaction conditions. After the reaction was complete, ethanol was evaporated to ~1–2 mL 30 mL EtOAc were added and extracted once with 5 mL of water (0.05N HCl). Solvent evaporation gave 1.6 grams (Yield 90%) of mono-acid II (FIG. 8).

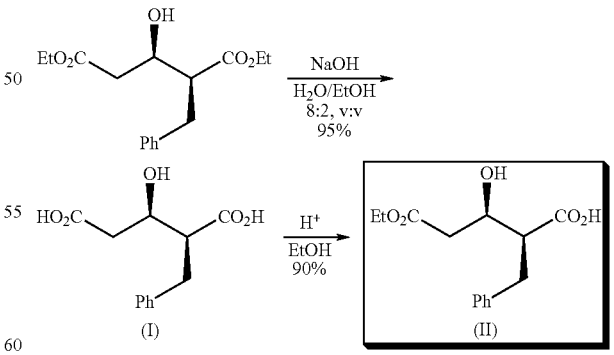

Figure 8: Synthesis of diethyl 2-benzyl-3-hydroxy ethyl-glutarate.

In a different method the first extraction was eliminated. According to this method, 4.5 g (0.015 mole) of diethyl 2-benzyl-3-hydroxy ethyl-glutarate are dissolved in 3 mL ethanol and were mixed with 15 mL of water containing 1.8 g (0.045 mole) of sodium hydroxide. After vigorous stirring at room temperature for 3 h HPLC analysis of a crude reaction mixture showed complete formation of the diacid I (FIG. 8). At this point the mixture was acidified to pH~2–3 with addition of 6M HCl solution and the solvent was evaporated to dryness under reduced pressure. The precipitate redissolved in 80 mL of ethanol, and, after filtering to remove the insoluble sodium chloride salts, it was concentrated under reduced pressure to 40 mL to azeotrope any remaining water from the mixture. A drop of concentrated HCl was then added, and the homogeneous mixture was stirred at 40 C for 14 h, where complete conversion to the more hindered mono acid II (FIG. 8) was obtained. Sometimes if long reaction times were allowed, 2–5% of the diester also formed. Solvent evaporation of the reaction mixture to dryness gave 3.9 g of the mono-acid product (yield 98%).

Example 23

Formation of the More Hindered Mono-Acid of diethyl 2-isobutyl 2-hydroxy ketoglutarate The first procedure of Example 22 was repeated except that diethyl 2-benzyl 2-hydroxy ketoglutarate was replaced with 2-isobutyl 2-hydroxy ketoglutarate. The product was the more hindered mono-acid that was isolated in 84% yield. It will be appreciated that the general procedure can be used in the practice of the present invention by one skilled in the art to produce a wide range of different more hindered mono-acid products.

Example 24

Rearrangement of mono-ethyl 2-benzyl 3-hydroxy glutarate (II. FIG. 8) with diphenylphosphoryl azide to the cyclic carbamate In 30 mL of toluene, 2 g (7.6 milimole) of the KRED-1008-produced mono-ethyl 2-benzyl 2-hydroxy ketoglutarate (II, FIG. 8) were dissolved along with 2 mL (9.3 milimole) and 0.8 (7.8 milimole) of triethylamine. The reaction was heated at 80 C and intense bubbling was observed. After 2.5 h at 80 C the temperature was decreased to 60 C and was left stirring for another 4 to 8 h. At the end of the reaction 30 mL of ethyl acetate were added to the reaction mixture, and was extracted once with 20 mL (0.25 N HCl) followed by extraction with 20 mL of saturated mono sodium carbonate (NaHCO3). The organic layer was then washed with brine and evaporated to dryness giving 2 g of an oily precipitate. Pure cyclic carbamate (FIG. 7) was obtained (1.2 g, 4.6 milimole) after silica gel purification in 60% isolated yield. Proton and carbon NMR as well as MS analysis all confirmed the correct structure. In addition careful proton decoupling and NOE experiments of the hydrogens present on the carbamate ring showed that their relative position is cis. Based on this result, the single diastereomer that was obtained in this reaction sequence using KRED 1008 can be assigned as having either the (3R, 4S) or (3S, 4R) absolute stereochemistry.

Example 25

Rearrangement of mono-ethyl 2-isobutyl 3-hydroxy glutarate (II, FIG. 8) with diphenylphosphoryl azide to the cyclic carbamate The procedure of Example 24 was repeated except that mono-ethyl 2-benzyl 3-hydroxy glutarate was replaced with mono-ethyl 2-isobutyl 3-hydroxy glutarate. The latter was synthesized from diethyl 2-isobutyl ketoglutarate after reduction with KRED 1001. As described above, proton NMR decoupling and NOE experiments showed that the hydrogens on the carbamate ring possessed the cis relative orientation, which is consistent with either (3R, 4S) or (3S, 4R) absolute stereochemistries. Thus, the single diastereomer obtained in this reaction sequence using KRED 1001 had the either (3R, 4S) or (3S, 4R) absolute stereochemistry.

Example 26

Alternative Rearrangement Conditions for mono-ethyl-2-benzyl-3-hydroxy glutarate Synthesis of the amine was also achieved under Hofmann rearrangement conditions starting from the corresponding amide. In 20 mL of methelene chloride containing a drop of dimethyl formamide, 1 g (3.8 millimole) of the hindered mono-acid of 2-benzyl 3-hydroxy glutarate (II, FIG. 8) was dissolved. After addition of 0.45 mL (5.1 millimole) of oxallyl chloride, the reaction was stirred at room temperature for 1 hour before ammonia gas started bubbling through a stainless steel needle immersed in the reaction solution. After one hour of bubbling, the solution was filtered and evaporated to dryness. Silica gel purification of the oily product obtained after solvent evaporation gave 0.5 g (50% yield) of the amide. Rearrangement of the amide was performed when 0.16 g of (0.6 millimole) were dissolved in 0.4 mL of acetonitrile and added to 0.4 mL of an aqueous solution containing 0.4 g (0.9 millimole) of [bis(trifluoroacetoxy)iodo]benzene [$(CF_3CO_2)_2PhI$]. After stirring the mixture for 4 hours at room temperature, 0.6 mL of a NaHCO3 saturated solution and 15 mL EtOAc are added. The mixture was filtered to remove the insoluble materials, and the two layers were allowed to separate. After isolation of the organic layer, drying with $Na_2SO_4$ and evaporation to dryness, 0.1 g (62% yield) of a cyclic carbamate as described in Examples 24 and 25 was obtained. The yields of amide formation can be improved by using a different method employing first reaction of the free acid with ethyl chloroformate followed by reaction with ammonia (*Organic Syntheses CV*8, 132). This reaction can be performed to synthesize the amide of the protected alcohol (synthesized as described in Examples 24 and 25) and then rearranged to the free amine with [bis(trifluoroacetoxy)iodo]benzene.

Example 27

Protection of the Hydroxy Group of mono-ethyl 2-benzyl 3-hydroxy glutarate (II, FIG. 8) as acetate After checking various methods for the acetylation of the alcohol in the presence of the free carboxyl group, it was identified that catalytic amounts of TMSOTf (trifluoromethanesulfonic acid trimethylsillilester) in the presence of acetic anhydride gave quantitative yields of the acetyl-protected alcohol. In a typical protocol, 0.5 g (1.9 milimole) of mono-ethyl 2-benzyl 3-hydroxy glutarate and 0.28 mL (2 milimole) of acetic anhydride and 5 μL of TMSOTf were dissolved in 10 mL of methylene chloride. The reaction was stirred at 4 C for 15 to 30 minutes before TLC analysis showed complete consumption of starting material. Evaporation of solvent and silica gel purification gave 0.5 g (5 milimole, 87% yield) of pure acetylated product.

Example 28

Protection of the Hydroxy Group of mono-ethyl 2-benzyl 3-hydroxy glutarate (II, FIG. 8) as tert-butyl dimethylsillyl (TBDMS)

In 5 mL of acetonitrile, 0.6 g (2.3 milimole) of mono-ethyl 2-benzyl 3-hydroxy glutarate and 0.6 g (4 milimole) tert-butyl dimethylsillylchloride (TBDMSCl) were dissolved. The mixture was cooled at −18 C for 10 minutes before 0.8 mL (5.2 milimole) of 1.8 diazabicyclo[5.4.0]undec-7-ene (DBU) were added. The reaction mixture was left to warm to 4 C in 2 hours and was stirred overnight at this temperature. At the end of the reaction 30 mL of ethyl acetate were added to the reaction mixture and extracted with 10 mL of 0.2 M HCl aqueous solution. Organic layer was dried with sodium sulfate, and evaporated to dryness. Pure protected alcohol (0.6 g, 69% yield) was isolated after silica gel chromatographic purification. It is important to note that if the reaction was not performed at low temperature, a different product (probably the protected carboxylic acid) was predominantly forming. A small amount of this impurity also formed under the aforementioned low temperature reaction conditions.

Example 29

Rearrangement of the TBDMS-Protected mono-ethyl 2-benzyl 3-hydroxy glutarate with diphenylphosphorylazide In 5 mL toluene 0.50 g (1.3 milimole) of TBDMS-protected mono-ethyl 2-benzyl 3-hydroxy glutarate along with 0.34 mL (1.6 milimole) diphenylphosphorylazide (DPPA) and 0.15 mL (1.44 milimole) of triethylamine (TEA) were dissolved. The reaction was heated at 75 C for 2 h and then it was allowed to cool at 60 C and stirred overnight. The next day, 4 mL of HCl (3M) were added to the mixture under vigorous stirring. The reaction was stirred for 30 minutes before 30 mL of ethyl acetate were added. The organic layer was removed and extracted once with 10 mL of a saturated solution of $NaHCO_3$. After washing with brine and drying with $NaSO_4$ the solvent was evaporated and an oily product was recovered. Silica gel purification gave 0.4 g of a compound that appeared to be (by proton NMR) the free amine. Mass spectrum analysis showed a parent ion peak (MW+1) of 324, which was consistent with the free acid and amine of the TBDMS-protected alcohol. Both the two aqueous solutions (HCl and $NaHCO_3$) that were recovered from the extraction of the organic layer were analyzed to identify if hydrolyzed amino acid product was present. Nothing was detected besides DPPA byproducts in the $NaHCO_3$ layer.

What is claimed is:

1. A compound having the formula $H_2N$—$CHR^1$—$CH(OH)$—$(CH_2)_n$—$COOH$, wherein n is 1 and $R^1$ is allyl.
2. A compound having the formula $H_2N$—$CHR^1$—$CH(OH)$—$(CH_2)_n$—$COOH$, wherein n is 1 and $R^1$ is propargyl.
3. A compound having the formula $H_2N$—$CHR^1$—$CH(OH)$—$(CH_2)_n$—$COOH$, wherein n is 1 and $R^1$ is 4-pyridyl.
4. A compound having the formula $H_2N$—$CHR^1$—$CH(OH)$—$(CH_2)_n$—$COOH$, wherein n is 1 and $R^1$ is 2-thienyl.
5. A compound having the formula $H_2N$—$CHR^1$—$CH(OH)$—$(CH_2)_n$—$COOH$, wherein n is 0 and $R^1$ is phenyl.
6. A compound having the formula $H_2N$—$CHR^1$—$CH(OH)$—$(CH_2)_n$—$COOH$, wherein n is 0 and $R^1$ is allyl.
7. A compound having the formula $H_2N$—$CHR^1$—$CH(OH)$—$(CH_2)_n$—$COOH$, wherein n is 0 and $R^1$ is propargyl.
8. A compound having the formula $H_2N$—$CHR^1$—$CH(OH)$—$(CH_2)_n$—$COOH$, wherein n is 0 and $R^1$ is 4-pyridyl.
9. A compound having the formula $H_2N$—$CHR^1$—$CH(OH)$—$(CH_2)_n$—$COOH$, wherein n is 0 and $R^1$ is thienyl.

* * * * *